United States Patent [19]

Oechsner

[11] 4,447,724

[45] May 8, 1984

[54] APPARATUS FOR THE CHEMICAL ANALYSIS OF SAMPLES

[75] Inventor: Hans Oechsner, Clausthal-Zellerfeld, Fed. Rep. of Germany

[73] Assignee: Leybold Heraeus GmbH, Cologne, Fed. Rep. of Germany

[21] Appl. No.: 337,647

[22] Filed: Jan. 7, 1982

Related U.S. Application Data

[63] Continuation of Ser. No. 139,087, Apr. 10, 1980, abandoned.

[30] Foreign Application Priority Data

Dec. 14, 1979 [DE] Fed. Rep. of Germany ....... 2950330

[51] Int. Cl.³ .................. H01J 49/26; H01J 49/10
[52] U.S. Cl. .................... 250/309; 250/281; 250/423 R; 250/505.1
[58] Field of Search ............... 250/251, 423 R, 309, 250/310, 281, 283, 424, 505.1

[56] References Cited

U.S. PATENT DOCUMENTS

| 3,084,281 | 4/1963 | Mills ............... 250/424 |
| 3,136,908 | 6/1964 | Weinman ........... 250/423 R |
| 3,376,469 | 4/1968 | Consoli et al. ..... 250/423 R |
| 3,660,655 | 5/1972 | Wardell ............ 250/281 |
| 3,665,185 | 5/1972 | Goff ............... 250/309 |
| 4,132,892 | 1/1979 | Wittmaack .......... 250/309 |
| 4,166,952 | 9/1979 | Colby et al. ....... 250/309 |
| 4,362,936 | 12/1982 | Hofmann et al. ..... 250/423 R |

FOREIGN PATENT DOCUMENTS 54-1248  9/1979  Japan ................... 250/251

Primary Examiner—Paul L. Gensler
Assistant Examiner—Carolyn E. Fields
Attorney, Agent, or Firm—Felfe & Lynch

[57] ABSTRACT

An apparatus for the chemical analysis of a sample ejects neutral and charged particles from the sample by ion bombardment from a primary ion source. An electric diaphragm passes only the ejected neutral particles for ioniziation in a plasma which is separate from the primary ion source and which serves only for the post-ionization of the neutral particles. The ionized particles are then analyzed by mass spectrometry. Charging of insulating samples by primary ions is prevented by rendering the diaphragm permeable to plasma electrons.

10 Claims, 1 Drawing Figure

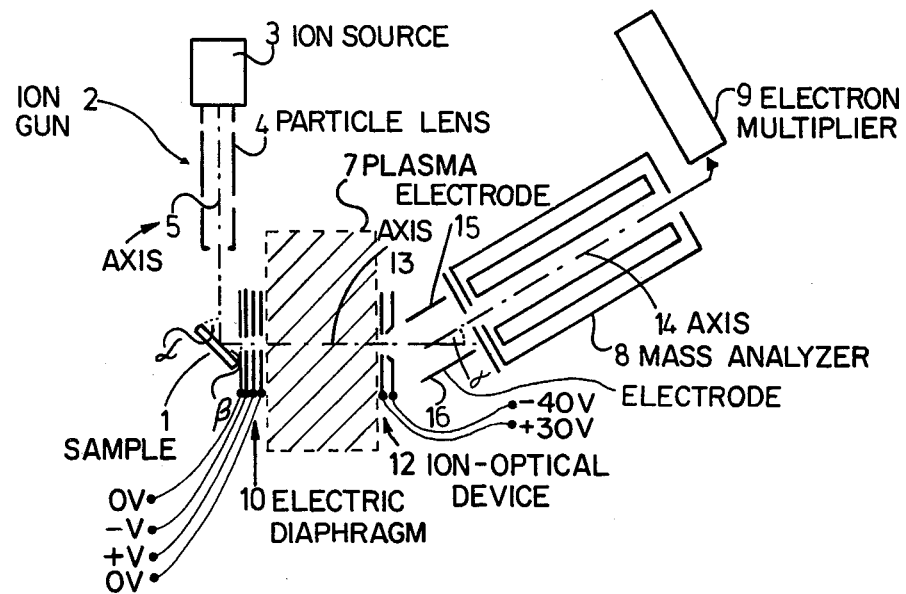

APPARATUS FOR THE CHEMICAL ANALYSIS OF SAMPLES

This is a continuation of Ser. No. 139,087 filed Apr. 10, 1980, now abandoned.

BACKGROUND OF THE INVENTION

The invention relates to apparatus for the chemical analysis of samples wherein neutral particles are ejected from the surface of the sample by ion bombardment, ionized in a plasma, and analyzed by mass spectrometry.

A method and apparatus of this type are known from PHYSICS LETTERS, vol. 3 (1972), pp. 211–212, and APPLIED PHYSICS, vol. 14 (1977), pp. 43–47. The method, known as SNMS (Sputtered Neutral Mass Spectrometry), offers the advantage over the SIMS (Secondary Ion Mass Spectrometry) method that, in the process of ionization of the particles to be analyzed, the nature of the sample surface exerts no influence. The SNMS method therefore permits quantitative determination of the chemical composition of the sample. With the SIMS method, the formation of secondary ions at the sample surface is dependent, in a complicated manner, upon the chemical nature of the surface, and variations in sensitivity of several powers of ten may occur. For this reason, while the SIMS method often permits high-sensitivity qualitative analyses to be made, quantitative analyses usually are not possible with this method.

In the known SNMS method, a high-frequency plasma, preferably an argon plasma, disposed in front of the sample has two functions. One of these is the production of primary ions which are accelerated onto the surface of the sample when a voltage is applied to the sample. The other function is the post-ionization of the neutral particles thereby ejected from the sample which then are detected by means of a mass spectrometer of any type, for example a quadrapole mass analyzer followed by a secondary electron multiplier or a Faraday cup. One disadvantage of the known SNMS method is that a high post-ionization probability of the neutral particles to be analyzed is always tied to a high bombardment-current density at the sample, and hence to a high removal rate. Another, is that it is not possible to achieve high lateral resolution since the primary ions of the plasma cannot be directed onto well-defined areas of the sample.

SUMMARY OF THE INVENTION

The object of the present invention thus is to overcome these drawbacks. In accordance with the invention, this is accomplished, in that the primary ions are produced in a separate ion source and that the plasma serves only for the post-ionization of the neutral particles. In a SNMS method carried out in this manner, the primry-ion production and the high-frequency plasma for post-ionization of the neutral particles are completely separate or decoupled. The samples can be bombarded in a well-aimed and reproducible manner by the use of a conventional ion source, such as a gas-discharge ion source and particle lens. With appropriate deflection of the primary-ion beam, it even becomes possible to sense the sample surface by the scanning method.

An advantageous apparatus comprises an ion source for bombardment of the sample with primary ions; means, not novel in themselves, for maintaining a plasma in proximity to the sample; and a mass spectrometer, which as such is known, following the plasma.

An advantageous improvement to an apparatus of this type comprises an electric diaphragm permeable to neutral particles and impermeable to charged particles disposed between the sample and the plasma. The diaphragm prevents charged particles ejected from the sample surface from permeating the plasma, entering the mass spectrometer and thus disturbing the measurement. At the same time, the diaphragm prevents ions or electrons from the plasma itself from reaching the sample and producing secondary effects there. For the analysis of samples which are electric insulators, the diaphragm may be rendered permeable to plasma electrons so as to prevent the sample from being charged by the primary ions.

Still more advantageously, a potential barrier is disposed between the plasma and the mass spectrometer to prevent plasma ions from entering the spectrometer detector system.

BRIEF DESCRIPTION OF THE DRAWING

Further advantages and details of the invention will now be described with reference to an embodiment of an apparatus which is illustrated diagrammatically in the accompanying drawing.

DETAILED DESCRIPTION OF THE INVENTION

In the embodiment shown, the sample is designated 1. An ion gun 2 consisting of an ion source 3 and, disposed in front thereof, a particle lens 4 is associated with the sample in such a way that the axis 5 of the ion gun forms an angle $\alpha$ of about 45° with the surface of the sample 1.

A high-frequency plasma 7 serves for the post-ionization of the neutral particles ejected from the surface of the sample 1. A mass spectrometer consisting of a quadrapole mass analyzer 8 and a secondary electron multiplier 9 is provided for the recording of the ionized neutral particles. The plasma 7 is produced by means of an electromagnetic high-frequency field, for example, with electron cyclotron wave resonance at a pressure around or below $10^{-3}$ millibars in an argon atmosphere. This technique of producing a plasma is known from PLASMA PHYSICS, vol. 16 (1974), pp. 835–844, for example. The plasma may be ignited simply by means of a pressure surge, such as a momentary pressure rise to $10^{-2}$ millibars. This expedient makes it possible to dispense with complex electric circuitry for ignition of the plasma.

Disposed between the sample 1 and the plasma 7 is an electric diaphragm 10 consisting of four aperture plates. This diaphragm is permeable to the neutral particles ejected from the sample but impermeable to the charged particles present, which are mostly of low energy. In this way, ions and electrons from the plasma 7 are prevented from impinging on the sample 1, and charged particles ejected from the sample are prevented from permeating the plasma and getting into the detector system 8 and 9. To accomplish this function, the apeture plates must be supplied with appropriate voltages. For examples, voltages of 0, −300, +60 and 0 volts are applied to the four aperture plates successively in the direction of the neutral-particle stream. For the analysis of samples which are electric insulators, the diaphragm may be rendered permeable to plasma electrons to prevent the sample from being charged by the primary ions.

The high-frequency plasma is followed by an ion optical device 12 which is supplied with such voltages that a retarding potential is produced in that region. This potential barrier serves to prevent plasma ions from entering the detector system 8 and 9. In the embodiment illustrated, two aperture plates with a voltage of about −40 and +30 volts are provided.

The electric diaphragm 10 and the ion device 12 are disposed on a common axis 13 which is perpendicular to the axis 5 of the ion gun 2, and are disposed so that the two axes 5 and 13 intersect in the region of the sample 1 to be analyzed. The surface of the sample 1 therefore also forms an angle $\beta$ of about 45° with the axis 13.

The axis 14 of the quadrapole mass analyzer 8 forms an angle $\gamma$ of about 30° with the axis 13. Tilting the quadrapole mass analyzer 8 in this manner results in a further reduction of the background. The electrodes 15 and 16 serve to deflect the particle beam into the mass analyzer 8.

It will be appreciated that the instant specification and the claims are set forth by way of illustration and not limitation, and that various modifications and changes may be made without departing from the spirit and scope of the present invention.

What is claimed is:

1. Apparatus for the chemical analysis of a sample, comprising:
    primary ion source means (3) bombarding the sample (1) with ions along an axis (5) for ejecting neutral and charged particles from the sample;
    electric diaphragm means (10) for being permeable along an axis (13) to the neutral particles ejected from the sample and impermeable at least to the charged particles ejected from the sample;
    plasma means (7) separate from the primary ion source means (3) and having a plasma along the axis (13) along which the electric diaphragm means (10) is permeable to the neutral particles and receiving the same therealong for ionizing the neutral particles with the plasma; and
    mass spectrometer means (8, 9) further along the axis (13) along which the electric diaphragm means is permeable than the plasma of the plasma means (7) to receive the now-ionized, formerly-neutral particles therefrom for performing the chemical analysis of the sample from the received ionized, formerly-neutral neutral particles thereof.

2. The apparatus of claim 1, wherein the electric diaphragm means comprises spaced plates each having an aperture aligned along the axis (13) for the permeability to the neutral particles therealong and electric potentials differing for the impermeability to the charged particles.

3. The apparatus of claim 2, wherein the plasma has electrons and the electric diaphragm means (10) further comprises means for permeability to at least some of the electrons from the plasma, whereby the electrons from the plasma can prevent insulating samples from being charged, the means comprising the electric potential on the plates.

4. An apparatus according to claim 2, wherein the axis of the ion source and the axis of the aperture plates are perpendicular to each other and the surface of the sample to be analyzed is located at the intersection of said axes.

5. An apparatus according to claim 4, wherein the surface of the sample forms an angle of about 45° with said axes.

6. An apparatus according to claim 2, further comprising means forming a potential barrier between the plasma means and the mass spectrometer means.

7. An apparatus according to claim 6, wherein the means forming the potential barrier comprises an ion optical device which precedes the mass spectrometer and is supplied with voltage to produce a retarding potential.

8. An apparatus according to claim 7, wherein the apertures of the plates of the electric diaphragm means and the ion optical device following the plasma are disposed on one axis (13) which forms an angle of about 30° with an axis into the mass spectrometer.

9. An apparatus according to claim 8, further comprising a particle lens following the primary ion source.

10. Apparatus for the chemical analysis of a sample comprising:
    a source for the ion bombardment of a sample, separate means for effective post-ionization of neutral particles ejected from the sample thereby, and a mass spectrometer, said apparatus being characterized
    by using the electron component of a low-pressure plasma maintained by electron cyclotron wave resonance as post-ionizing medium,
    by positioning an electric diaphragm comprising a row of aperture plates at different electric potential between the sample and the plasma, said diaphragm being permeable to neutral particles but impermeable to charged particles and including means for effecting same to be permeable in one arbitrary direction to particles having arbitrary charge, and
    by applying a retarding electric potential barrier between the plasma and the mass spectrometer.

* * * * *